US012127821B2

(12) United States Patent
Deno et al.

(10) Patent No.: US 12,127,821 B2
(45) Date of Patent: Oct. 29, 2024

(54) BLOOD PRESSURE AND ELECTROCARDIOGRAPH MEASUREMENT DEVICE AND METHOD

(71) Applicant: OMRON HEALTHCARE Co., Ltd., Kyoto (JP)

(72) Inventors: Toru Deno, Kyoto (JP); Takahiro Hamaguchi, Kyoto (JP); Masahiko Yumoto, Kyoto (JP); Takanobu Yamauchi, Kyoto (JP); Yasushi Matsuoka, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 886 days.

(21) Appl. No.: 17/176,747

(22) Filed: Feb. 16, 2021

(65) Prior Publication Data

US 2021/0161399 A1    Jun. 3, 2021

Related U.S. Application Data

(63) Continuation of application No. PCT/JP2019/029026, filed on Jul. 24, 2019.

(30) Foreign Application Priority Data

Aug. 22, 2018  (JP) ................. 2018-155466

(51) Int. Cl.
*A61B 5/0225*  (2006.01)
*A61B 5/00*   (2006.01)
*A61B 5/318*  (2021.01)

(52) U.S. Cl.
CPC .......... *A61B 5/0225* (2013.01); *A61B 5/318* (2021.01); *A61B 5/681* (2013.01); *A61B 5/742* (2013.01)

(58) Field of Classification Search
CPC ........ A61B 5/0225; A61B 5/022; A61B 5/318
See application file for complete search history.

(56) References Cited

U.S. PATENT DOCUMENTS

| 2001/0012916 A1* | 8/2001 | Deuter ................. A61B 5/742 |
| | | 600/494 |
| 2005/0171444 A1* | 8/2005 | Ono ..................... A61B 5/0002 |
| | | 600/490 |

(Continued)

FOREIGN PATENT DOCUMENTS

| CN | 203436321 | 2/2014 |
| EP | 2689721 A1 | 1/2014 |

(Continued)

OTHER PUBLICATIONS

International Preliminary Report on Patentability issued Feb. 25, 2021 in International (PCT) Patent Application No. PCT/JP2019/029026.

(Continued)

*Primary Examiner* — Michael R Bloch
(74) *Attorney, Agent, or Firm* — Wenderoth, Lind & Ponack, L.L.P.

(57) ABSTRACT

A measurement device includes a pressure acquisition unit configured to acquire pressure information representing pressure in a pressing cuff, a cuff pressure control unit configured to control, based on the pressure information, the pressure in the pressing cuff during each of a pressurizing step of pressurizing the pressing cuff, a pressurized state maintaining step of maintaining the pressing cuff in a pressurized state after end of the pressurizing step, and a depressurizing step of depressurizing the pressing cuff after end of the pressurized state maintaining step, a blood pressure calculation unit configured to calculate a blood pressure of a user based on the pressure information, and an (Continued)

electrocardiographic measurement unit configured to measure an electrocardiogram of the user during the pressurized state maintaining step.

10 Claims, 7 Drawing Sheets

(56) References Cited

U.S. PATENT DOCUMENTS

| | | | |
|---|---|---|---|
| 2006/0264771 A1 | 11/2006 | Lin et al. | |
| 2007/0100247 A1* | 5/2007 | Platt | A61B 5/02233 |
| | | | 600/490 |
| 2008/0033310 A1* | 2/2008 | Yu | A61B 5/02208 |
| | | | 600/493 |
| 2010/0298655 A1* | 11/2010 | McCombie | A61B 5/0002 |
| | | | 600/301 |
| 2014/0031662 A1 | 1/2014 | Chou | |
| 2015/0119654 A1* | 4/2015 | Martin | A61B 5/6898 |
| | | | 600/513 |
| 2016/0235325 A1 | 8/2016 | Chou | |
| 2017/0245773 A1* | 8/2017 | Wiesel | A61B 5/361 |
| 2018/0085058 A1* | 3/2018 | Chakravarthi | G16H 40/67 |
| 2018/0200140 A1* | 7/2018 | Ganske | B32B 27/40 |
| 2018/0333056 A1 | 11/2018 | Chou | |
| 2019/0159676 A1* | 5/2019 | Murphy | A61B 5/0022 |
| 2019/0269914 A1* | 9/2019 | Moaddeb | A61H 23/0245 |

FOREIGN PATENT DOCUMENTS

| | | |
|---|---|---|
| JP | 2001-204696 | 7/2001 |
| JP | 2004-65336 A | 3/2004 |
| JP | 2006-326293 A | 12/2006 |
| JP | 2007-195693 A | 8/2007 |
| JP | 2014-36843 A | 2/2014 |
| JP | 2015-77229 A | 4/2015 |
| WO | 2016/119656 | 8/2016 |

OTHER PUBLICATIONS

Notice of Reasons for Refusal issued Oct. 11, 2022 in corresponding Japanese Patent Application No. 2018-155466, with English translation.

Notice of Reasons for Refusal issued Jul. 26, 2022 in corresponding Japanese Patent Application No. 2018-155466 with machine translation.

Notice of First Examination Opinion issued Nov. 29, 2023 in corresponding Chinese Patent Application No. 201980050192.8, with English machine translation.

\* cited by examiner

BLOOD PRESSURE AND ELECTROCARDIOGRAPH MEASUREMENT DEVICE AND METHOD

CROSS-REFERENCE TO RELATED APPLICATIONS

This application is the U.S. national stage application filed pursuant to 35 U.S.C. 365(c) and 120 as a continuation of International Patent Application No. PCT/JP2019/029026, filed Jul. 24, 2019, which application claims priority from Japanese Patent Application No. 2018-155466, filed Aug. 22, 2018, which applications are incorporated herein by reference in their entireties.

TECHNICAL FIELD

The invention relates to a measurement device and a measurement method that enable blood pressure measurement and electrocardiographic measurement, and a non-transitory recording medium in which a measurement program enabling blood pressure measurement and electrocardiographic measurement is recorded, for example.

BACKGROUND ART

Patent Document 1 discloses a blood pressure measurement device. The blood pressure measurement device detects a pulse wave signal of a patient using a pulse wave sensor and calculates blood pressure based on the detected pulse wave signal.

CITATION LIST

Patent Literature

Patent Document 1: JP 2015-77229 A

SUMMARY OF INVENTION

Technical Problem

On the other hand, there is a need for electrocardiographic measurement in addition to blood pressure measurement. In this type of measurement device, a pair of electrodes is provided as electrocardiographic measurement electrodes. In a case where either of the pair of electrodes is not in proper contact with a target measurement site of a user, useful electrocardiographic measurement results may not be obtained.

In light of the circumstances described above, an object of one aspect is to provide a measurement device, a measurement method, and a measurement program that can properly achieve blood pressure measurement and electrocardiographic measurement.

Solution to Problem

In order to solve the problems described above, the present invention adopts the following measures, for example.

That is, a measurement device according to an example of the present disclosure includes a pressure acquisition unit configured to acquire pressure information representing pressure in a pressing cuff, a cuff pressure control unit configured to control, based on the pressure information, the pressure in the pressing cuff during each of a pressurizing step of pressurizing the pressing cuff, a pressurized state maintaining step of maintaining the pressing cuff in a pressurized state after end of the pressurizing step, and a depressurizing step of depressurizing the pressing cuff after end of the pressurized state maintaining step, a blood pressure calculation unit configured to calculate a blood pressure of a user based on the pressure information, an electrocardiographic measurement unit configured to measure an electrocardiogram of the user during the pressurized state maintaining step, and a first electrode and a second electrode as a pair of electrocardiographic electrodes, and the cuff pressure control unit is configured to maintain the pressure in the pressing cuff during the pressurized state maintaining step at a pressure at the end of the pressurizing step, and the second electrode is disposed at a position where the second electrode contacts the skin at an attachment site of the user in a state where the pressing cuff is attached to the user.

According to the configuration described above, an electrocardiogram is measured during the pressurized state maintaining step provided between the pressurizing step and the depressurizing step for the pressing cuff. Here, during the pressurized state maintaining step, the pressing cuff is expanded to cause the electrocardiographic measurement electrode to reliably contact an attachment site of the user and sufficiently closely contact the attachment site. Accordingly, an electrocardiogram in a proper attachment state can be measured, and proper electrocardiographic measurement results can be obtained.

In the measurement device according to the above-described example, the cuff pressure control unit is configured to set a duration of the pressurized state maintaining step equal to or longer than a measurement time required to obtain an electrocardiographic waveform useful for diagnosis.

According to the above-described configuration, the electrocardiogram in the proper attachment state can be measured, and the electrocardiographic waveform useful for diagnosis can be reliably acquired.

In the measurement device according to the above-described example, the cuff pressure control unit is configured to maintain the pressure in the pressing cuff during the pressurized state maintaining step at a constant value.

In the measurement device according to the example above, the blood pressure calculation unit is configured to calculate the blood pressure of the user based on a fluctuation in pressure in the pressing cuff during the pressurizing step for the pressing cuff or the depressurizing step for the pressing cuff, the fluctuation being acquired from the pressure information.

In the measurement device according to the example described above, the electrocardiographic measurement unit includes an electrocardiographic detection information acquisition unit configured to acquire detection information representing a current value flowing through the heart of a user between a pair of electrocardiographic measurement electrodes, and a generation unit configured to generate an electrocardiographic waveform reflecting the detection information during the pressurized state maintaining step for the pressing cuff based on the detection information acquired by the electrocardiographic detection information acquisition unit.

In the measurement device according to the above-described example, the electrocardiographic detection information acquisition unit is configured to acquire the detection information during a period from the pressurizing step through the depressurizing step, and the generation unit is configured to generate an electrocardiographic waveform reflecting only the detection information that is acquired during the pressurized state maintaining step, from among the detection information being acquired.

According to the above-described configuration, electrocardiographic waveforms reflecting only the detection results obtained in the proper attachment state.

In the measurement device according to the above-described example, the electrocardiographic detection information acquisition unit is configured to acquire, as the detection information, only the current value during the pressurized state maintaining step.

According to the above-described configuration, electrocardiographic measurement is performed only in the proper attachment state to reduce a burden on a patient.

The measurement device according to the example described above further includes, as the electrocardiographic measurement electrodes, a first electrode disposed at a position where the first electrode does not contact the skin at an attachment site of the user in a state where the measurement device is attached to the user, a second electrode disposed at a position where the second electrode contacts the skin at the attachment site of the user in a state where the measurement device is attached to the user, and the electrocardiographic detection information acquisition unit is configured to detect, as the detection information, a current flowing through the heart of the user between the first electrode and the second electrode.

The measurement device according to the example described above further includes a body including a first surface provided with a display unit and a second surface corresponding to a rear surface with respect to the first surface, and the pressing cuff configured to externally compress the attachment site of the user by being pressurized in a state where the pressing cuff is attached to the user, and the first electrode is disposed on the first surface of the body and the second electrode is disposed on the second surface of the body.

In the measurement device according to the example described above, the second electrode is attached to the user, and in a state where the pressing cuff is pressurized, the second electrode is pressed by the pressing cuff to closely contact the attachment site of the user.

Advantageous Effects of Invention

According to the present invention, a measurement device and a measurement method that can properly measure blood pressure and an electrocardiogram, and a non-transitory recording medium in which a measurement program that can properly measure blood pressure and an electrocardiogram is recorded are provided.

DESCRIPTION OF EMBODIMENTS

Now, with reference to the drawings, embodiments are described. Note that, in the following description, constituent elements having the same function and configuration are denoted with a shared reference symbol. Further, when a plurality of constituent elements having a shared reference symbol are distinguished from one another, distinguishment is made by adding additional symbols following the shared reference symbol. Note that, when there is no particular need in distinguishing a plurality of constituent elements, the plurality of constituent elements are denoted only with a shared reference symbol without an additional symbol.

1. Application Example

Figure 1:
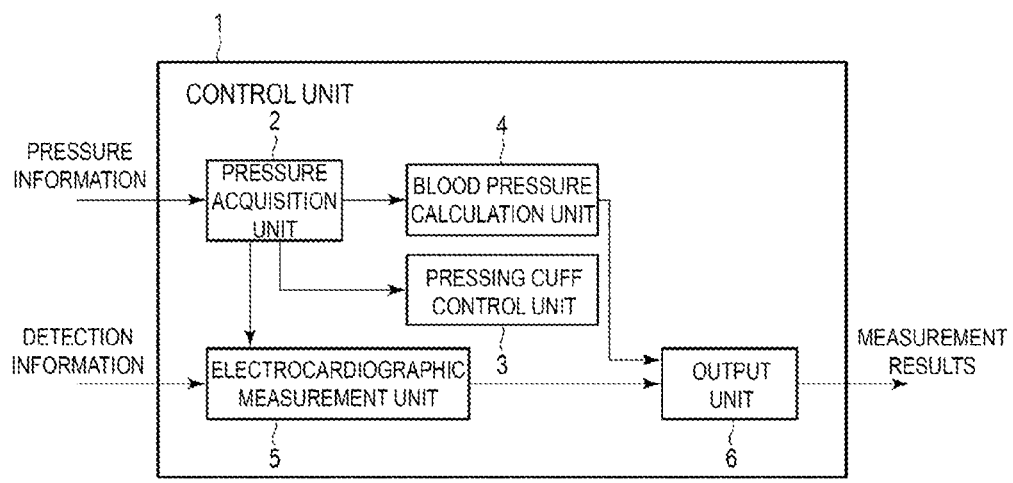
FIG. 1 is a block diagram illustrating an example of the functional configuration of a measurement device according to an application example.

First, with reference to FIG. 1, an example of a measurement device to which the present invention is applied will be described.

The blood pressure measurement device 1 is an example of a measurement device that can measure the blood pressure and electrocardiogram of a user. The blood pressure measurement device 1 is attached to an attachment site of the user. The attachment site is, for example, a wrist, an upper arm, or the like. The blood pressure measurement device 1 executes a side effect management process based on a side effect management program. The side effect management program is an example of an electrocardiographic measurement program. As illustrated in FIG. 1, the blood pressure measurement device 1 includes a pressure acquisition unit 2, a pressing cuff control unit 3, a blood pressure calculation unit 4, an electrocardiographic measurement unit 5, and an output unit 6.

The pressure acquisition unit 2 acquires pressure information. The pressure information includes the pressure in the pressing cuff (cuff pressure). The pressure acquisition unit 2 acquires pressure information from a pressure sensor provided in the pressing cuff, for example.

The pressing cuff control unit 3 controls the state of the pressing cuff based on the pressure information. The pressing cuff control unit 3 controls the state of the pressing cuff, for example, by controlling driving of a pump supplying a fluid to the pressing cuff and an exhaust valve provided in the pressing cuff. The pressing cuff control unit 3 expands and pressurizes the pressing cuff, for example, by supplying a fluid from the pump to the pressing cuff. The pressing cuff control unit 3 contracts and depressurizes the pressing cuff, for example, by discharging the fluid from the pressing cuff. The pressing cuff control unit 3 is an example of a cuff pressure control unit.

The blood pressure calculation unit 4 calculates the blood pressure of the user based on the pressure information. For example, an oscillometric method is used for the calculation of the blood pressure performed by the blood pressure calculation unit 4. The blood pressure calculation unit 4 calculates the blood pressure based on, for example, a fluctuation in pressure in the pressing cuff during the pressurizing step for the pressing cuff. The blood pressure calculation unit 4 may calculate the blood pressure based on a fluctuation in pressure in the pressing cuff during the depressurizing step for the pressing cuff. The blood pressure calculated by the blood pressure calculation unit 4 is a systolic blood pressure, a diastolic blood pressure, or other index.

The electrocardiographic measurement unit 5 measures an electrocardiogram of the user based on detection information. The detection information includes, for example, a current value flowing through the heart of the user between a pair of electrocardiographic measurement electrodes. The electrocardiographic measurement unit 5 generates an electrocardiographic waveform based on the detection information.

The electrocardiographic measurement unit 5 sets the pressurized state maintaining step between the pressurizing step for the pressing cuff and the depressurizing step for the pressing cuff. The electrocardiographic measurement unit 5 generates an electrocardiographic waveform generated based on the detection information during the pressurized state maintaining step as electrocardiographic information.

The pressurized state maintaining step starts after the end of the pressurizing step, and ends before the start of the depressurizing step. In other words, the electrocardiographic measurement unit 5 measures an electrocardiogram of the user from the time when the pressurization of the pressing cuff is stopped until the depressurization of the pressing cuff is started. The electrocardiographic measurement unit 5 maintains the pressure in the pressing cuff at a constant value during the pressurized state maintaining step. In other words, the electrocardiographic measurement unit 5 maintains the pressing cuff in a pressurized state during the pressurized state maintaining step. For example, during the pressurized state maintaining step, the electrocardiographic measurement unit 5 performs control to maintain the pressure in the pressing cuff to the pressure at the end of the pressurizing step.

The duration of the pressurized state maintaining step is set, for example, equal to or longer than to a measurement time required to obtain an electrocardiographic waveform useful for diagnosis.

In an example, the electrocardiographic measurement unit 5, for example, acquires detection information during a period from the pressurizing step through the pressurized state maintaining step and the depressurizing step, and generates an electrocardiographic waveform reflecting only the detection information that is acquired during the pressurized state maintaining step, from among the acquired detection information. In another example, the electrocardiographic measurement unit 5, for example, acquires only the detection information during the pressurized state maintaining step, and generates an electrocardiographic waveform reflecting the acquired detection information.

The output unit 6 outputs the blood pressure information calculated by the blood pressure calculation unit 4 and the electrocardiographic information generated by the electrocardiographic measurement unit 5. In this way, blood pressure measurement results and electrocardiographic measurement results are displayed on the display device.

In blood pressure measurement and electrocardiographic measurement, the pressurizing step for the pressing cuff is started in a state where the blood pressure measurement device 1 is attached to the attachment site of the user. As the pressing cuff is pressurized, the pressing cuff is expanded to compress the attachment site of the user. Then, in a state where the attachment site of the user is sufficiently compressed by the pressing cuff, the pressurization of the pressing cuff is stopped, and the pressurizing step ends. In a state where the pressurization of the pressing cuff is stopped, the electrocardiographic measurement electrodes are pressurized from the outside toward the attachment site of the user by the pressing cuff being expanded, and thus the electrocardiographic measurement electrodes reliably contact the attachment site of the user and sufficiently closely contact the attachment site. In a state where the attachment site of the user is not sufficiently compressed by the pressing cuff, the electrocardiograph electrodes may not sufficiently closely contact the attachment site of the user.

With the configuration described above, electrocardiogram is measured during the pressurized state maintaining step in which the pressing cuff is maintained in the pressurized state. As described above, between the pressurizing step and the depressurizing step, the pressing cuff maintained being pressurized, and the pressing cuff is expanded to cause the electrocardiographic measurement electrodes to reliably contact the attachment site of the user and sufficiently closely contact the attachment site. Accordingly, the blood pressure measurement device 1 can measure an electrocardiogram in a proper attachment state. As a result, proper electrocardiographic measurement results can be obtained.

2. First Embodiment

A first embodiment of the measurement device according to the application example described above will be described below. In the following, a blood pressure measurement system including a blood pressure measurement device will be described below.

2.1 Overall Configuration Example

Figure 2:
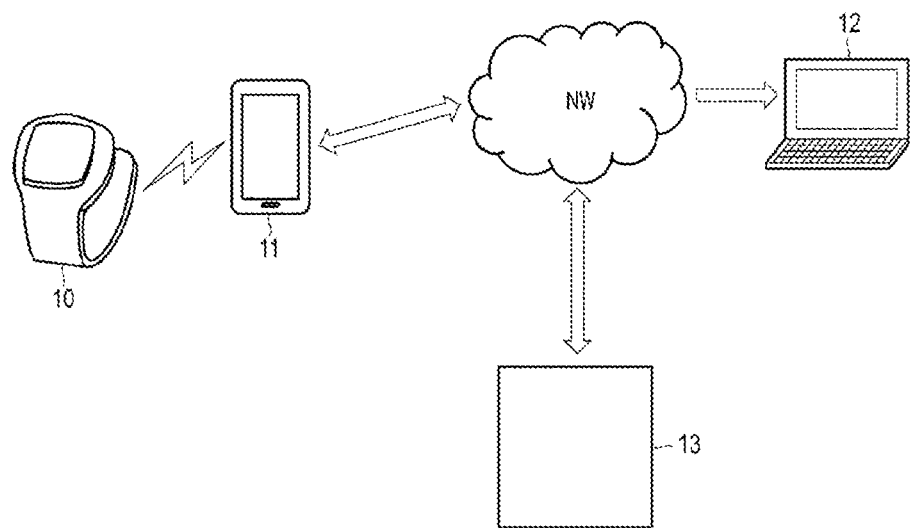
FIG. 2 is a schematic diagram illustrating a configuration of a blood pressure measurement system including the measurement device according to a first embodiment.

FIG. 2 is a diagram schematically illustrating an example of an application scenario of the blood pressure measurement system according to the present embodiment. The blood pressure measurement system according to the present embodiment is a system for displaying blood pressure measurement results, electrocardiographic measurement results, and other information on a display screen.

The blood pressure measurement system includes a blood pressure measurement device 10. The blood pressure measurement device 10 is an example of the measurement device. In the example in FIG. 2, the blood pressure measurement system further includes a portable terminal 11, a physician terminal 12, and a server 13. A plurality of the blood pressure measurement devices 10 and a plurality of the portable terminals 11 may be provided. In this case, the blood pressure measurement devices 10 and the portable terminals 11 are connected by near-field wireless communication or wired communication. The portable terminal 11 can be connected to a server 13 via a network NW. The portable terminal 11 may be further connected to the physician terminal 12 via the network NW. The physician terminal 12 and the server 13 can be connected via a network NW, such as the Internet. A plurality of the physician terminals 12 may be provided. For communication between the physician terminal 12 and the server 13, near-field wireless communication or wired communication, which are not via the network NW, may be applied. Thus, the blood pressure measurement device 10 can be connected to the server 13 (and the physician terminal 12) via the portable terminal 11. That is, the blood pressure measurement device 10 can communicate with the server 13 (and the physician terminal 12) via the portable terminal 11.

The blood pressure measurement device 10 is a device that can be attached to any measurement location. The measurement location may be, for example, the wrist, the upper arm, or the like. The blood pressure measurement device 10 can measure a blood pressure value of the user at a measurement location. The blood pressure measurement device 10 can transmit the blood pressure information including the measurement results of the blood pressure value and the like to the portable terminal 11. Additionally, the blood pressure measurement device 10 can measure the electrocardiographic waveform of the user. The blood pressure measurement device 10 can transmit, to the portable terminal 11, the electrocardiographic information including the electrocardiographic waveform being measured. The blood pressure measurement device 10 includes a clock function and can transmit the blood pressure information and the electrocardiographic information to the portable terminal 11 in association with a measured date/time.

For example, the portable terminal 11 is a terminal that can be carried by the user. The portable terminal 11 receives the blood pressure information and the electrocardiographic information from the blood pressure measurement device 10. The portable terminal 11 can save the received blood pressure information and electrocardiographic information along with the measured date/time, for example. Additionally, the portable terminal 11 can transfer the saved blood pressure information and electrocardiographic information to the server 13 in association with the measured date/time as appropriate.

The physician terminal 12 is a terminal operable by an administrator such as a physician. The administrator such as a physician, for example, provide medical consultation to the user to diagnose the medical condition of the user based on test data and the like. The physician terminal 12 can receive test data from a test device (not illustrated) or the like in a hospital, and present the test data to the administrator. The diagnosis information related to the user is input to the physician terminal 12 by an operation of the administrator. The physician terminal 12 can transmit the input diagnosis information to the server 13.

The server 13 is a server computer that accumulates information transmitted from the portable terminal 11, the physician terminal 12, and the like. The accumulated information is stored as an electronic medical chart, for example.

2.2 Hardware Configuration Examples

Description will be given of an example of a hardware configuration and an example of structure of the blood pressure measurement device in the blood pressure measurement system according to the present embodiment.

2.2.1 Hardware Configuration Example of Blood Pressure Measurement Device

Figure 3:
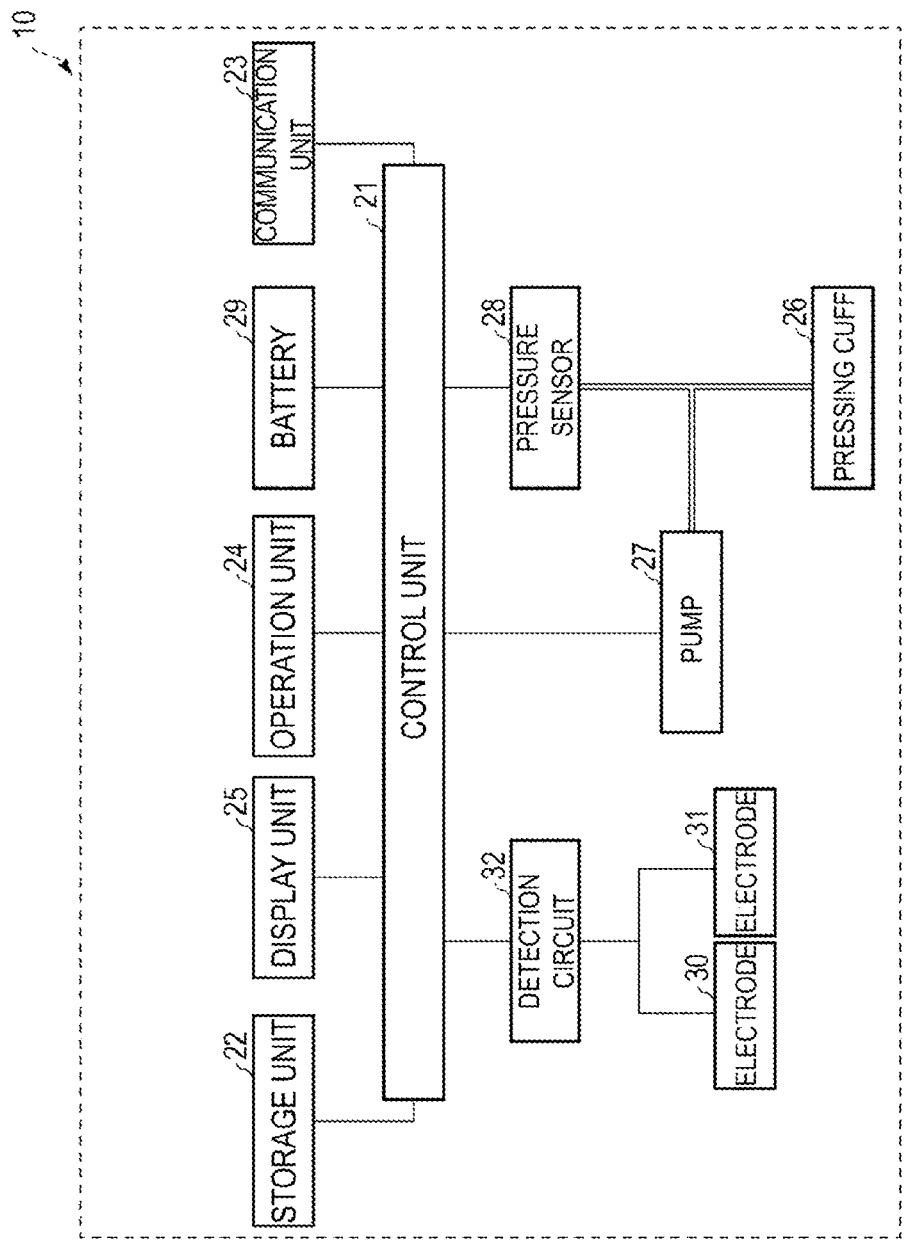
FIG. 3 is a block diagram illustrating an example of the hardware configuration of the measurement device according to the first embodiment.

First, a hardware configuration example of the blood pressure measurement device 10 according to the present embodiment will be described. FIG. 3 is a block diagram illustrating an example of the hardware configuration of the blood pressure measurement device 10 according to the present embodiment. As illustrated in FIG. 3, the blood pressure measurement device 10 according to the present embodiment includes a control unit 21, a storage unit 22, a communication unit 23, an operation unit 24, a display unit 25, a pressing cuff 26, a pump 27, a pressure sensor 28, a battery 29, a first electrode 30, a second electrode 31, and a detection circuit 32. The blood pressure measurement device 10 may further include an acceleration sensor and a temperature/humidity sensor.

The control unit 21 includes a central processing unit (CPU), a random-access memory (RAM), a read-only memory (ROM), and the like, and controls each constituent element in accordance with information processing. Additionally, the control unit 21 includes a clock (not illustrated), and has a function of acquiring a current date/time. The control unit 21 may have a function of displaying the acquired date/time on the display unit 25.

The control unit 21 drives the pump 27 to expand and contract the pressing cuff 26. In addition, the control unit 21 controls the opening and closing of the exhaust valve provided in the pressing cuff 26. In addition, the control unit 21 supplies electrical energy from the battery 29 to each of the first electrode 30 and the second electrode 31, and applies different voltages to the first electrode 30 and the second electrode 31. In addition, the control unit 21 generates blood pressure information and electrocardiographic information based on the measurement results obtained by the pressure sensor 28 and the detection circuit 32. The blood pressure information includes, for example, the blood pressure value and the like of the user. The electrocardiographic information includes an electrocardiographic waveform and the like. Each of the blood pressure information and the electrocardiographic information is associated with the measured date/time, which is based on the current date/time acquired by the clock. Additionally, each of the blood pressure information and the electrocardiographic information may further be associated with a device ID for uniquely identifying the blood pressure measurement device 10.

In addition, the control unit 21 executes electrocardiographic measurement processing based on an electrocardiographic measurement program. The electrocardiographic measurement processing by the control unit 21 will be described below. The electrocardiographic measurement program is a program for causing the control unit 21 to execute the electrocardiographic measurement processing. The electrocardiograph measurement program is stored in the storage unit 22, for example. The electrocardiographic measurement program is an example of the measurement program.

The storage unit 22 is, for example, an auxiliary storage device such as a solid state drive, for example. In a case where the blood pressure measurement device 10 is configured as a somewhat large device rather than a small device such as a watch type, the storage unit 22 may be a hard disk drive. The storage unit 22 stores programs executed by the control unit 21, the blood pressure information, the electrocardiographic information, setting information, and the like.

The communication unit 23 is a communication interface configured to perform communication with the portable terminal 11. The communication unit 23 transmits, to the portable terminal 11, the blood pressure information, pulse information, the electrocardiographic information, and the like, for example. Near-field wireless communication such as Bluetooth (trade name), for example, can be applied to communication with the portable terminal 11 made by the communication unit 23, but no such limitation is intended. For example, communication performed by the communication unit 23 may adopt communication via the network NW such as a local area network (LAN) or wired communication through use of a communication cable.

For example, the operation unit 24 includes a user interface such as a touch panel and an operation button. The operation unit 24 detects an operation performed by the user via the user interface, and outputs a signal indicating the content of the operation to the control unit 21.

The display unit 25 includes, for example, a display screen (for example, a liquid crystal display (LCD), an electroluminescent (EL) display, or the like), an indicator, and the like. The display unit 25 displays information in accordance with a signal from the control unit 21, and notifies the information to the user. The display unit 25 can display, for example, blood pressure values, electrocardiographic waves, and the like. The display unit 25 is an example of a display screen.

The pressing cuff 26 is, for example, a band-like air bag. The pressing cuff 26 is supplied with a fluid to externally compress the attachment site of the user.

The pump 27 is, for example, a piezoelectric pump. The pump 27 may supply the fluid to the pressing cuff 26. The fluid supplied from the pump 27 to the pressing cuff 26 is, for example, air. An exhaust valve controllably opened and closed depending on the state of the pump 27 is attached to the pump 27. The exhaust valve is closed in a case where the pump 27 is in an on state, sealing air within the pressing cuff 26. On the other hand, the exhaust valve is opened in a case where the pump 27 is in an off state, discharging air in the pressing cuff 26 into the atmosphere. In addition, the exhaust valve includes the function of a check valve. Thus, backflow of air discharged from inside the pressing cuff 26 is prevented.

The pressure sensor 28 is, for example, a piezoresistive pressure sensor. The pressure sensor 28 detects the pressure in the pressing cuff 26 through a flexible tube. The pressure sensor 28 outputs detection results to the control unit 21.

The control unit 21 calculates the blood pressure value of the user based on the pressure in the pressing cuff 26 detected by the pressure sensor 28. The blood pressure value includes representative indices such as, for example, a systolic blood pressure and a diastolic blood pressure. At this time, the control unit 21 calculates the blood pressure of the user on the spot (non-continuously) for a predetermined period of time, for example, based on the detection results from the pressure sensor 28. The control unit 21 generates time series data of the pressure value using the detection results from the pressure sensor 28, and calculates the blood pressure of the user for a predetermined period of time based on time series data of the pressure value. Thus, the pressure sensor 28 is an example of a non-continuous measurement type blood pressure sensor. For example, the non-continuous measurement type blood pressure sensor may adopt a method of detecting a pulse wave by applying a pressure to a blood vessel using the pressing cuff 26 as a pressure sensor (oscillometric method).

The battery 29 is, for example, a rechargeable secondary battery. The battery 29 stores power to be supplied to each element mounted in the blood pressure measurement device 10. The battery 29 supplies power to the control unit 21, the storage unit 22, the communication unit 23, the operation unit 24, the display 25, the pressing cuff 26, the pump 27, the pressure sensor 28, the battery 29, the first electrode 30, the second electrode 31, and the detection circuit 32.

The first electrode 30 and the second electrode 31 are electrodes used for measuring the electrocardiographic waveform. The first electrode 30 and the second electrode 31 function as electrodes having different potentials by being supplied with power from the battery 29. In a state where each of the first electrode 30 and the second electrode 31 is in contact with the skin of the user, the power is supplied to each of the first electrode 30 and the second electrode 31, and thus current flows through the heart of the user between the first electrode 30 and the second electrode 31. Each of the first electrode 30 and the second electrode 31 is an example of the electrocardiographic measurement electrode.

The first electrode 30 is provided in a portion of the blood pressure measurement device 10 that is exposed to the outside in a state where the blood pressure measurement device 10 is attached to the user. Additionally, the first electrode 30 is positioned in a position where the first electrode 30 can be operated by a user in a state where the blood pressure measurement device 10 is attached to the attachment site. The first electrode 30 does not contact the skin at the attachment site of the user in a state where the blood pressure measurement device 10 is attached to the user. In electrocardiographic measurement, the user presses the first electrode 30 with a finger using an arm opposite to the arm to which the blood pressure measurement device 10 is attached.

The second electrode 31 is provided on the blood pressure measurement device 10 at a position facing the skin at the attachment site in a state where the blood pressure measurement device 10 is attached to the attachment site. The second electrode 31 is disposed at a position where the blood pressure measurement device 10 contacts the skin at the attachment site of the user in a state where the blood pressure measurement device 10 is attached to the user.

The detection circuit 32 detects a current flowing through the heart of the user between the first electrode 30 and the second electrode 31. The detection circuit 32 outputs an electrical signal indicating a current value of the detected current to the control unit 21. The set of the first electrode 30, the second electrode 31, and the detection circuit 32 is an example of an electrocardiographic sensor. The set of the first electrode 30 and the second electrode 31 is an example of the electrocardiograph measurement electrodes.

2.2.2 Structure Example of Blood Pressure Measurement Device

Figure 4:
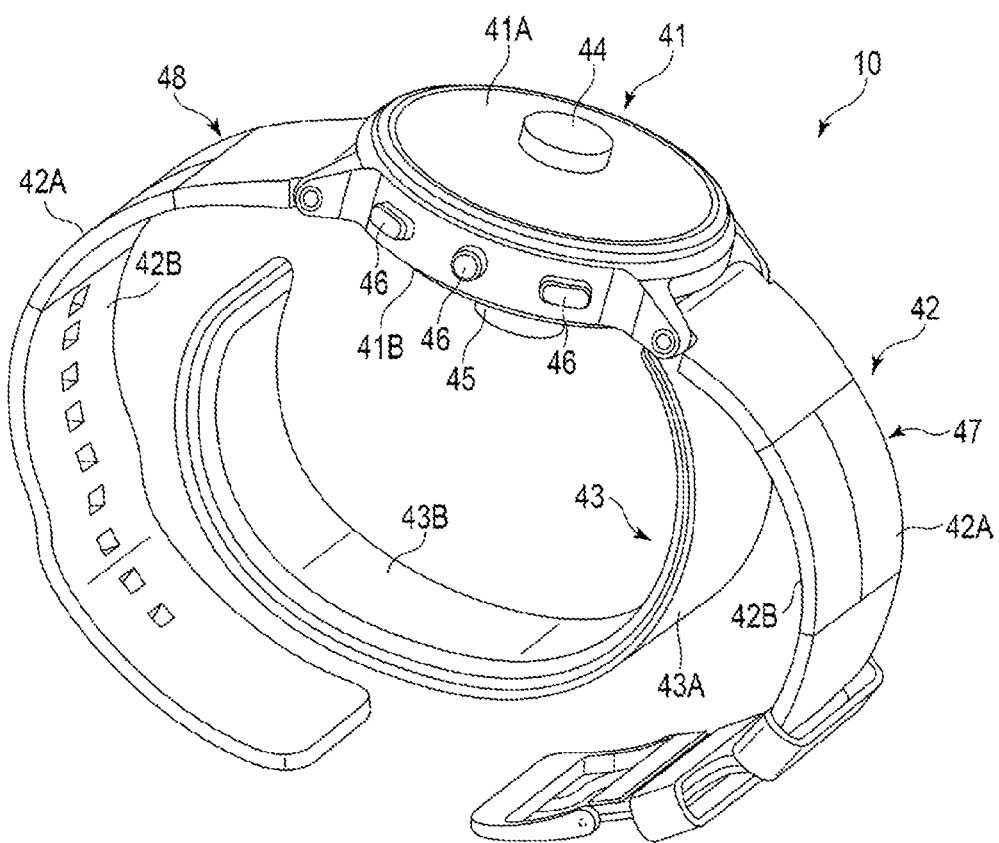
FIG. 4 is a diagram illustrating an example of a configuration of the measurement device according to the first embodiment.

A structure example of the blood pressure measurement device 10 corresponding to the measurement device according to the present embodiment will be described. FIG. 4 is a perspective view illustrating an example of the structure of the blood pressure measurement device 10. In an example in FIG. 4, the blood pressure measurement device 10 is a wristwatch type wearable device attached to the wrist of the user. As illustrated in FIG. 4, the blood pressure measurement device 10 includes a body 41, a belt 42, a cuff unit 43, a conductor 44, and a conductor 45. The wrist is an example of the attachment site. The conductor 44 and the conductor 45 function as electrocardiographic measurement electrodes.

The body 41 has, for example, a substantially short cylindrical shape. A pair of belts 42 are attached to the side surface of the body 41. Each belt of the pair of belts 42 is attached at one end to the side surface of the body 41. The pair of belts 42 are connected to the body 41 on opposite side surfaces of the body 41.

The body 41 is configured such that a plurality of elements of the blood pressure measurement device 10 can be mounted in the body 41. The body 41 includes, for example, the control unit 21, the storage unit 22, the communication unit 23, the operation unit 24, the display unit 25, the battery 29, the first electrode 30, the second electrode 31, and the detection circuit 32.

The body 41 includes a front surface 41A and a rear surface 41B. The front surface 41A and the rear surface 41B face opposite each other. The blood pressure measurement device 10 is attached to the wrist of the user such that the front surface 41A faces outward. In a state where the blood pressure measurement device 10 is attached to the wrist of the user, the rear surface 41B faces inward and faces the skin at the wrist of the user. The front surface 41A is an example of a first surface. The rear surface 41B is an example of a second surface.

A display screen is provided on the front surface 41A, for example. The front surface 41A functions as the display unit 25. The display screen is a liquid crystal display (LCD), for example. The display screen may be an organic electro luminescence (EL) display. Additionally, the display screen may include a light emitting diode (LED). It is sufficient that the display screen includes a function of displaying various types of information, and limitation to the above-described configuration is not intended.

A plurality of push buttons 46 are provided on the side surface of the body 41. The push buttons 46 function as the operation unit 24. The push buttons 46 are used to input various instructions for the blood pressure measurement device 10. For example, one of the push buttons 46 is used to input an instruction to start blood pressure measurement. Additionally, for example, another one of the push buttons 46 is used to input an instruction to start blood pressure measurement and electrocardiographic measurement.

The blood pressure measurement device 10 may include, instead of the push buttons 46, a pressure sensitive type (resistance type) or a proximity type (capacitance type) touch panel type switch, as the operation unit 24. It is sufficient that the operation unit 24 includes a function of inputting various instructions for the blood pressure measurement device 10, and limitation to the above-described configuration is not intended.

The belt 42 is configured such that the belt 42 can be externally wrapped around the wrist of the user. The belt 42 includes a first belt portion 47 and a second belt portion 48. The first belt portion 47 and the second belt portion 48 are each formed in band-like shape. The first belt portion 47 and the second belt portion 48 are formed of, for example, a resin material and have flexibility. One end of the first belt portion 47 is pivotally connected to the side surface of the body 41. A fastening member is attached to the other end of the first belt portion 47. One end of the second belt portion 48 is pivotally connected to a portion of the side surface of the body 41 opposite to the portion to which the first belt portion 47 is connected. The first belt portion 47 and the second belt portion 48 are fastened together by engaging the second belt portion 48 with the fastening member of the first belt portion 47. By fastening the first belt portion 47 and the second belt portion 48 together, the blood pressure measurement device 10 is attached to the wrist of the user.

The belt 42 includes an outward facing surface 42A and an inward facing surface 42B. The outward facing surface 42A and the inward facing surface 42B face opposite each other. In a state where the blood pressure measurement device 10 is attached to the wrist of the user, the outward facing surface 42A of the belt 42 faces outward. Additionally, in a state where the blood pressure measurement device 10 is attached to the wrist of the user, the inward facing surface 42B of the belt 42 faces inward.

The cuff unit 43 is a band-like air bag. The cuff unit 43 is pivotally attached at one end to the side surface of the body 41. The cuff unit 43 is disposed facing the inward facing surface 42B of the belt 42. The other end of the cuff unit 43 is a free end. Thus, the cuff unit 43 is freely spaced apart from the inner circumferential surface of the belt 42. In a state where the blood pressure measurement device 10 is attached to the wrist H of the user, the cuff unit 43 is extended between the inward facing surface 42B of the belt 42 and the wrist of the user.

The cuff unit 43 functions as the pressing cuff 26. The cuff unit 43 is connected to the pump 27 through a flexible tube, for example. The cuff unit 43 is supplied with a fluid from the body 41 through the flexible tube. The fluid is, for example, air. The cuff unit 43 is expanded when the cuff unit 43 is supplied with the fluid from the pump 27 of the body 41. Additionally, the cuff unit 43 is contracted when the air is discharged from inside the cuff unit 43. When the fluid is supplied to the cuff unit 43 in a state where the blood pressure measurement device 10 is attached, the expansion of the cuff unit 43 compresses the wrist of the user.

The cuff unit 43 includes the outward facing surface 43A and the inward facing surface 43B. The inward facing surface 43B faces the side opposite to the side faced by the outward facing surface 43A. The outward facing surface 43A of the cuff unit 43 faces the inward facing surface 42B of the belt 42. The inward facing surface 43B faces the skin of the wrist in a state where the blood pressure measurement device 10 is attached to the wrist. Specifically, a part of the inward facing surface 43B forms a part of a portion of the pressure measurement device 10 that faces the skin at the attachment site in a state where the pressure measurement device 10 is attached to the attachment site. Thus, in an example in FIG. 4, in a state where the blood pressure measurement device 10 is attached, the rear surface 41B of the body 41 and the inward facing surface 43B of the cuff unit 43 face the skin of the wrist of the user.

The conductor 44 is attached to the front surface 41A of the body 41. The conductor 44 has electrical conductivity. The conductor 44 is electrically connected to the battery 29 inside the body 41. When power from the battery 29 is supplied to the conductor 44, the conductor 44 functions as the first electrode 30. In a state where the blood pressure measurement device 10 is attached to the attachment site, the first electrode 30 may be disposed at a position where the first electrode 30 is exposed to the outside. Accordingly, the conductor 44 may be disposed, for example, on the side surface of the body 41, the outward facing surface 42A of the belt 42, or the like.

The conductor 45 is attached to the rear surface 41B of the body 41. The conductor 45 has electrical conductivity. The conductor 45 is electrically connected to the battery 29 inside the body 41. When power from the battery 29 is supplied to the conductor 45, the conductor 45 functions as the second electrode 31. In a state where the blood pressure measurement device 10 is attached to the attachment site, the second electrode 31 may be disposed at a position where the second electrode 31 faces the skin at the attachment site. Accordingly, the conductor 45 may be disposed on the inward facing surface 43B of the cuff unit 43, for example.

2.3 Functional Configuration Examples

Now, an example of a functional configuration of the blood pressure measurement system according to the present embodiment will be described.

Figure 5:
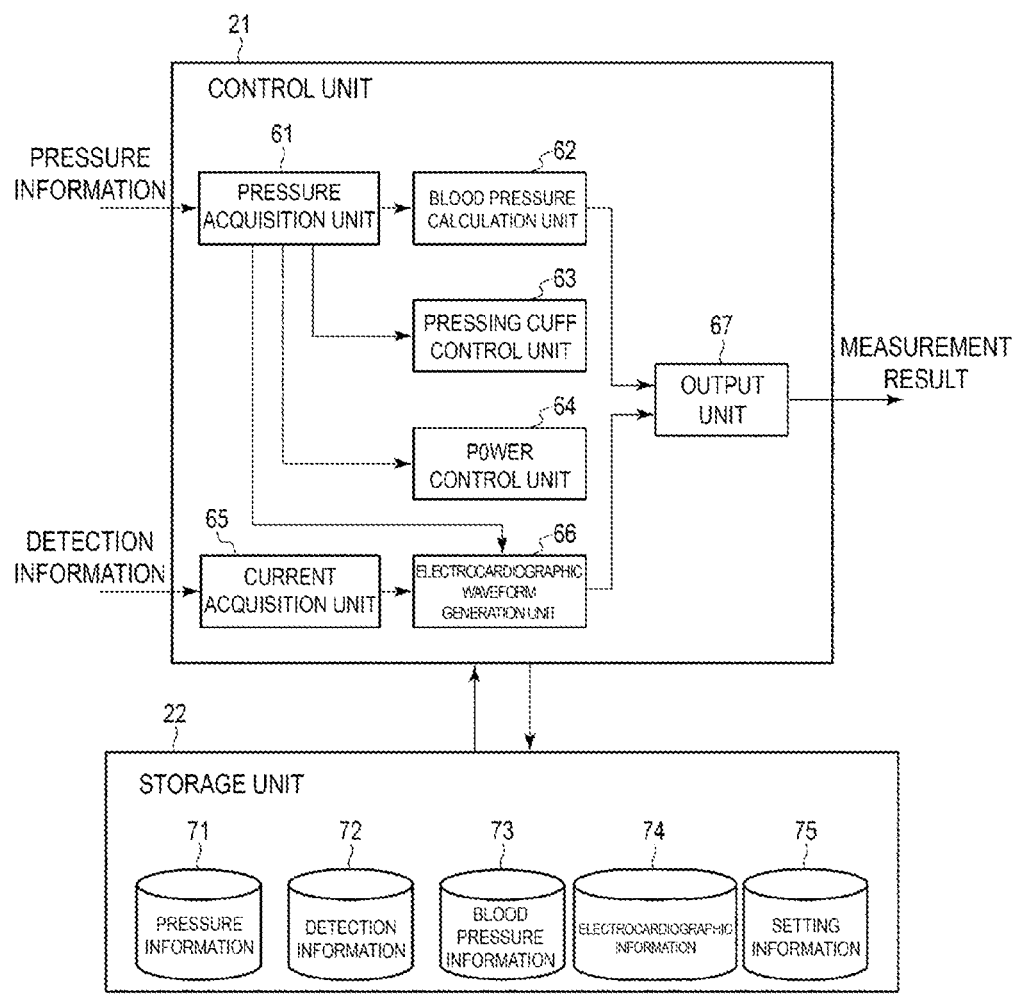
FIG. 5 is a block diagram illustrating an example of the functional configuration of a blood pressure measurement circuit as an example of the measurement device according to the first embodiment.

2.3.1 Functional Configuration Example of Blood Pressure Measurement Device FIG. 5 is a block diagram schematically illustrating an example of a functional configuration of the blood pressure measurement device 10 of the blood pressure measurement system according to the present embodiment.

The control unit 21 of the blood pressure measurement device 10 deploys the electrocardiographic measurement program stored in a non-volatile memory of the storage unit 22 into a volatile memory of the storage unit 22. Then, by interpreting and executing the electrocardiography measurement program deployed into the volatile memory, the control unit 21 functions as a pressure acquisition unit 61, a blood pressure calculation unit 62, a pressing cuff control unit 63, a power control unit 64, a current acquisition unit 65, an electrocardiographic waveform generation unit 66, and the output section 67.

The volatile memory of the storage unit 22 functions as a pressure information storage unit 71, a detection information storage unit 72, a blood pressure information storage unit 73, an electrocardiographic information storage unit 74, and a setting information storage unit 75.

The pressure information storage unit 71 stores pressure information. The pressure information includes the pressure in the pressing cuff 26 detected by the pressure sensor 28.

Detection information detected by the detection circuit 32 is stored in the detection information storage unit 72. The detection information includes a current value flowing between the first electrode 30 and the second electrode 31.

The blood pressure information storage unit 73 stores blood pressure information. The blood pressure information includes a blood pressure value. The blood pressure value is a systolic blood pressure, a diastolic blood pressure, or other index. The blood pressure information can also include a measured date/time and a measurement location for each blood pressure value.

The electrocardiographic information storage unit 74 stores electrocardiographic information. The electrocardiographic information includes electrocardiographic waveform display data and the like.

Pieces of setting information used in the electrocardiographic measurement processing are stored in the setting information storage unit 75. The setting information includes a threshold value and the like used in the electrocardiographic measurement processing.

The pressure acquisition unit 61 acquires the pressure (cuff pressure) in the pressing cuff 26. The pressure acquisition unit 61 acquires the pressure in the pressing cuff 26 from the pressure sensor 28, for example. The pressure acquisition unit 61 stores the acquired pressure in the pressure information storage unit 71 of the storage unit 22 as pressure information.

The blood pressure calculation unit 62 calculates the blood pressure value based on the pressure information acquired by the pressure acquisition unit 61. The blood pressure value is, for example, a systolic blood pressure, a diastolic blood pressure, or other index. The blood pressure calculation unit 62 uses the oscillometric method to calculate the blood pressure value based on a fluctuation in pressure during compression of the attachment site, i.e., from a fluctuation in pressure during the pressurizing step or the depressurizing step for the pressing cuff 26. The blood pressure calculation unit 62 stores the calculated blood pressure value in the blood pressure information storage unit 73 of the storage unit 22 as blood pressure information.

The pressing cuff control unit 63 controls the state of the pressing cuff 26 based on the pressure information acquired by the pressure acquisition unit 61. The pressing cuff control unit 63 controls the amount of fluid supplied to the pressing cuff 26, for example, by controlling the driving of the pump 27. The pressing cuff control unit 63 is an example of a cuff pressure control unit.

The power control unit 64 controls power supplied from the battery 29 to the first electrode 30 and the second electrode 31. The power control unit 64 may control the power supplied to the first electrode 30 and the second electrode 31 based on the pressure information acquired by the pressure acquisition unit 61.

The current acquisition unit 65 acquires detection information. The detection information includes, for example, the current value of the current detected by the detection circuit 32. The current acquisition unit 65 stores the acquired detection information in the detection information storage unit 72 of the storage unit 22. The current acquisition unit 65 is an example of an electrocardiographic detection information acquisition unit. The current acquisition unit 65 is an example of an electrocardiographic measurement unit.

The electrocardiographic waveform generation unit 66 generates the electrocardiographic waveform display data based on the pressure information acquired by the pressure acquisition unit 61 and the detection information acquired by the current acquisition unit 65. The electrocardiographic waveform display data is image data to be displayed on the display unit 25. The electrocardiographic waveform display data is stored in the electrocardiographic information storage unit 74 of the storage unit 22 as electrocardiographic information. The electrocardiographic waveform generation unit 66 is an example of a generation unit. Additionally, the electrocardiographic waveform generation unit 66 is an example of an electrocardiographic measurement unit.

The electrocardiographic waveform generation unit 66 sets an electrocardiographic measurement time. The electrocardiographic measurement time is the time between the end of the pressurizing step and the start of the depressurizing step for the pressing cuff 26 in the electrocardiographic measurement processing. Thus, the electrocardiographic waveform generation unit 66 sets the pressurized state maintaining step between the pressurizing step and the depressurizing step. The electrocardiographic measurement time is, for example, the measurement time required to obtain an electrocardiographic waveform useful for diagnosis. The electrocardiographic measurement time is, for example, 10 seconds. The electrocardiographic measurement time is an example of the duration of the pressurized state maintaining step. The electrocardiographic measurement time is stored in the setting information storage unit 75 of the storage unit 22, for example.

The electrocardiographic waveform generation unit 66 acquires detection information during a period from the pressurizing step through the depressurizing step. The electrocardiographic waveform generation unit 66 determines, among the acquired detection results, the detection results that correspond to the pressurizing step and the depressurizing step to be noise. The electrocardiographic waveform generation unit 66 excludes the detection results determined to be noise, and generates the electrocardiographic waveform display data. Thus, for example, the detection results from the detection circuit 32 during the pressurizing step and the depressurizing step for the pressing cuff 26 are not reflected in the electrocardiographic waveform display data. Accordingly, the electrocardiographic waveform generation unit 66 generates the electrocardiographic waveform display data based only on the current value detected by the detection circuit 32 during the pressurized state maintaining step.

The output unit 67 outputs, to the display unit 25, the blood pressure information calculated by the blood pressure calculation unit 62, and causes the display unit 25 to display blood pressure measurement results. In addition, the output unit 67 outputs, to the display unit 25, the electrocardiographic waveform display data generated by the electrocardiographic waveform generation unit 66, and causes the display unit 25 to display electrocardiographic measurement results.

2.4 Operation Examples

Now, an operation example of the blood pressure measurement system according to the present embodiment will be described. Note that the processing procedure described below is merely an example, and each process may be changed to the extent possible. Further, in the processing procedure described below, steps can be omitted, substituted, and added in accordance with the embodiment as appropriate.

2.4.1 Operation Example of Blood Pressure Measurement System

Figure 6:
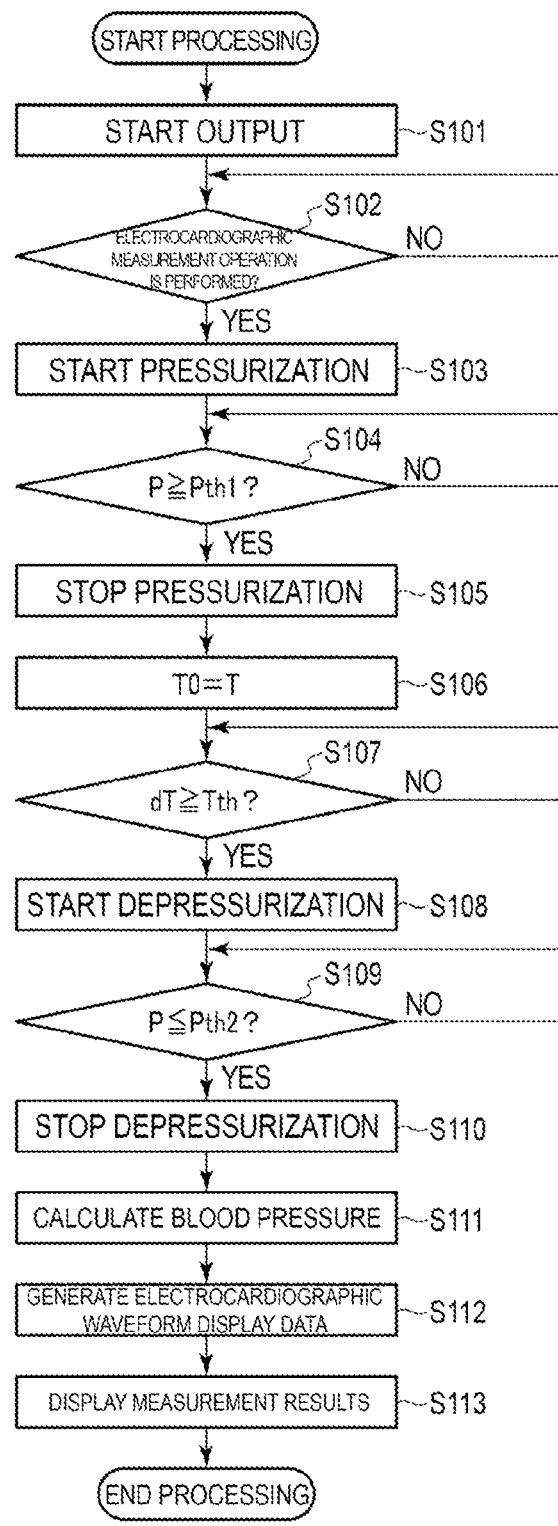
FIG. 6 is a flowchart illustrating an example of a processing procedure for electrocardiographic measurement using the blood pressure measurement system including the blood pressure measurement circuit as an example of the measurement device according to the first embodiment.

FIG. 6 is a flowchart illustrating an example of a procedure of processing by the control unit 21 of the blood pressure measurement device 10, in electrocardiographic measurement using the blood pressure measurement system according to the present embodiment. The control unit 21 starts the electrocardiographic measurement processing based on, for example, the input of an instruction to start electrocardiographic measurement at the operation unit 24 of the blood pressure measurement device 10 in a state where the blood pressure measurement device 10 is attached to the attachment site of the user. In the electrocardiographic measurement processing, the blood pressure and electrocardiogram of the user are measured, and the blood pressure measurement results and the electrocardiographic measurement results are displayed on the display unit 25.

Figure 7:
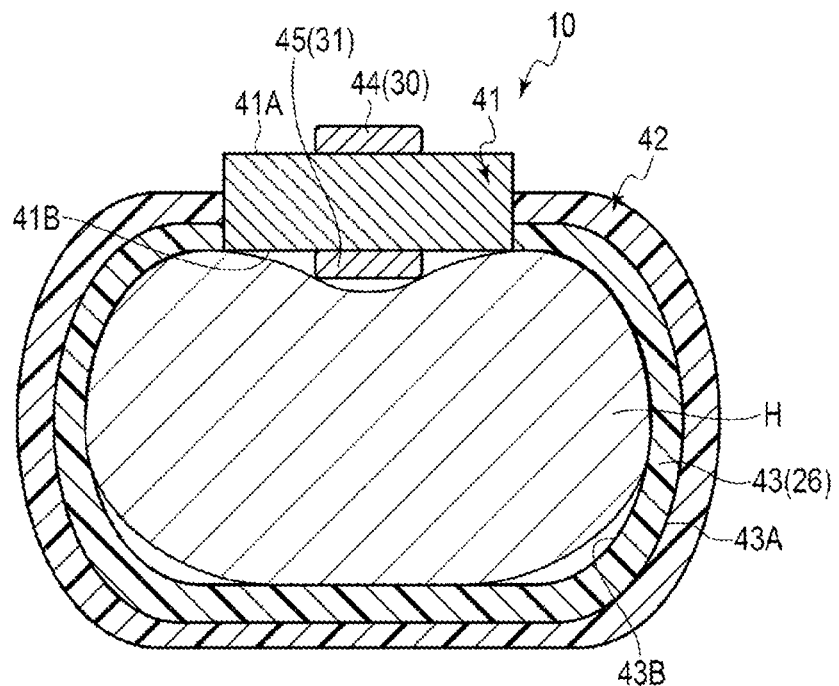
FIG. 7 is a schematic diagram illustrating an example of a state in which the measurement device according to the first embodiment is attached to an attachment site of a user and electrocardiographic measurement processing is not performed.
Figure 8:
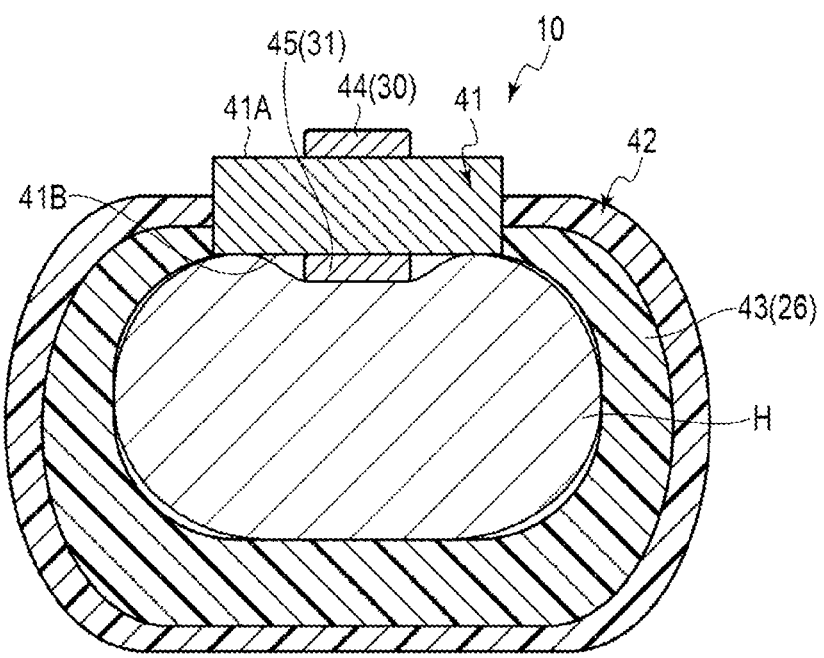
FIG. 8 is a schematic diagram illustrating an example of a state in which the measurement device according to the first embodiment is attached to the attachment site of the user and pressurization of the pressing cuff is stopped in the electrocardiographic measurement processing.

FIGS. 7 and 8 are diagrams illustrating a state in which the blood pressure measurement device 10 illustrated in the example in FIG. 4 is attached to the wrist H of the user. FIG. 7 illustrates a state in which the pressing cuff 26 is not expanded in the electrocardiographic measurement processing. FIG. 8 illustrates a state in which the pressing cuff 26 is expanded in the electrocardiographic measurement processing. The wrist H is an example of the attachment site.

In the electrocardiographic measurement processing, first, the control unit 21 starts supplying power to the first electrode 30 and the second electrode 31 (S101). At this time, the control unit 21 may, for example, cause the display unit 25 to provide display prompting the user to perform an electrocardiographic measurement operation. The control unit 21 causes the display unit 25 to display, for example, "Start electrocardiographic measurement," "Press measurement button," or the like as display prompting the user to perform an electrocardiographic measurement operation. Instead of the display on the display unit 25, a sound, a lighting display, or the like may be used to prompt the user to perform the electrocardiographic measurement operation.

In an electrocardiographic measurement operation, in a state where the blood pressure measurement device 10 is attached to the attachment site, the user causes the first electrode 30 to contact a finger of the arm to which the blood pressure measurement device 10 is not attached. By performing the electrocardiographic measurement operation in a state where the second electrode 31 is in proper contact with the skin at the attachment site of the user, a current flows between the first electrode 30 and the second electrode 31 through the heart of the user. The detection circuit 32 detects the current flowing between the first electrode 30 and the second electrode 31 and outputs to the control unit 21.

Then, the control unit 21 determines whether the electrocardiographic measurement operation is performed by the user (S102). By this way, the control unit 21 determines whether an operation for starting electrocardiographic measurement is performed. The control unit 21 waits until the electrocardiographic measurement operation is performed. For example, the control unit 21 determines that the electrocardiographic measurement operation is performed based on the current waveform detected by the detection circuit 32 exhibiting a predetermined behavior.

When the electrocardiographic measurement operation is performed (S102—Yes), the control unit 21 starts pressurizing the pressing cuff 26 (S103). At this time, the control unit 21 starts pressurizing the pressing cuff 26 by starting supplying of air from the pump 27 to the pressing cuff 26. This starts the pressurizing step of the pressing cuff 26.

Then, the control unit 21 determines whether a pressure P detected by the pressure sensor 28 is equal to or higher than a first threshold value Pth1 (S104). In other words, the control unit 21 determines whether the pressure in the pressing cuff 26 is equal to or higher than a predetermined value. The first threshold value Pth1 is a predetermined pressure value at the end of pressurization of the pressing cuff 26 in the blood pressure measurement. The first threshold value Pth1 is stored in the setting information storage unit 75 of the storage unit 22, for example.

In a case where the pressure P is lower than the first threshold value Pth1 (S104—No), the control unit 21 repeats the determination in S104. In other words, the control unit 21 continues the pressurization of the pressing cuff 26 until the pressure in the pressing cuff 26 is equal to or higher than a predetermined value. In a case where the pressure P is equal to or higher than the first threshold value Pth1 (S104—Yes), the control unit 21 determines that the wrist H of the user is sufficiently compressed by the pressing cuff 26. Then, the control unit 21 stops pressurizing the pressing cuff 26 (S105). At this time, the control unit 21 stops supplying air from the pump 27 to the pressing cuff 26, thus stopping pressurization of the pressing cuff 26. Accordingly, the pressurizing step for the pressing cuff 26 ends.

As illustrated in the example in FIG. 7, in a state where the cuff unit 43 is not expanded, the conductor 45 does not sufficiently closely contact the wrist H of the user. That is, in a state where the pressing cuff 26 is not sufficiently pressurized, the second electrode 31 does not sufficiently closely contact the attachment site of the user. With the cuff unit 43 pressurized, expansion of the cuff unit 43 causes the conductor 45 to be externally pressed inward against the skin at the wrist H of the user. This increases the contact strength with which the conductor 45 contacts the wrist H of the user.

As illustrated in the example in FIG. 8, in a case where the pressure P in the cuff unit 43 is equal to or higher than the first threshold value Pth1, the conductor 45 contacts the wrist H of the user with sufficient contact strength. In other words, in a state where the pressing cuff 26 is sufficiently pressurized, the second electrode 31 properly contacts the attachment site of the user.

Then, the control unit 21 sets, as a reference time T0, the time at which the pressure P is determined to be equal to or higher than the first threshold value Pth1 (S106). The reference time T0 is the time when the pressurizing step for the pressing cuff 26 ends. The control unit 21 continuously acquires an elapsed time dT from the reference time T0.

Then, the control unit 21 determines whether the elapsed time dT is equal to or longer than a threshold value Tth (S107). The threshold value Tth is an example of an electrocardiographic measurement time, and is an example of the duration of the pressurized state maintaining step. The threshold value Tth is stored in the setting information storage unit 75 of the storage unit 22, for example. By determining whether the elapsed time dT is equal to or longer than the threshold value Tth, the control unit 21 determines whether or not the electrocardiographic measurement time has elapsed during the pressurized state maintaining step. During the pressurized state maintaining step, the state is maintained in which the second electrode 31 is in proper contact with the attachment site of the user.

In a case where the elapsed time dT is shorter than the threshold Tth (S107—No), the control unit 21 repeats the determination in S107. In other words, the control unit 21 waits until the electrocardiographic measurement time elapses during the pressurized state maintaining step.

In a case where the elapsed time dT is equal to or longer than the threshold value Tth (S107—Yes), the control unit 21 determines that the electrocardiographic measurement time has elapsed during the pressurized state maintaining step. Then, the control unit 21 starts the depressurization of the pressing cuff 26 (S108). At this time, the control unit 21 starts the depressurization of the pressing cuff 26 by causing air to flow out of the pressing cuff 26. This starts the depressurizing step for the pressing cuff 26. As air flows out of the pressing cuff 26, the pressing cuff 26 in the expanded state is contracted, and the compression, by the pressing cuff 26, of the wrist H of the user is correspondingly relaxed.

Then, the control unit 21 determines whether the pressure P detected by the pressure sensor 28 is equal to or lower than a second threshold value Pth2 (S109). In other words, the control unit 21 determines whether the pressure in the pressing cuff 26 is equal to or lower than a predetermined value. The second threshold value Pth2 is a predetermined pressure value at the end of depressurizing step for the pressing cuff 26 in the blood pressure measurement. The second threshold value Pth2 is stored in the setting information storage unit 75 of the storage unit 22, for example.

In a case where the pressure P is higher than the second threshold value Pth2 (S109—No), the control unit 21 repeats the determination in S109. In other words, the control unit 21 continues the depressurization of the pressing cuff 26 until the pressure in the pressing cuff 26 is equal to or lower than the predetermined value. In a case where the pressure P is equal to or lower than the second threshold value Pth2 (S109—Yes), the control unit 21 stops the depressurization of the pressing cuff 26 (S110). At this time, the control unit 21 stops the depressurization of the pressing cuff 26 by stopping the flow of air out of the pressing cuff 26. This ends the depressurizing step for the pressing cuff 26.

Then, the control unit 21 calculates the blood pressure value based on the pressure P in the pressing cuff 26 detected by the pressure sensor 28 (S111). The control unit 21 uses the oscillometric method to calculate the systolic blood pressure and the diastolic blood pressure based on, for example, a fluctuation in pressure P in the pressing cuff 26 obtained between S103 and S110. The control unit 21 may calculate other index such as an average value or a representative value of the blood pressure based on the systolic blood pressure and the diastolic blood pressure. The control unit 21 stores the calculated blood pressure value in the blood pressure information storage unit 73 of the storage unit 22.

Note that the blood pressure calculation processing in S111 may be continuously performed during the period from the start of the pressurizing step for the pressing cuff 26 (S103) until the end of the depressurizing process for the pressing cuff 26 (S110). The blood pressure calculation processing in S111 may be performed based only on the detection results for the pressure P in the pressing cuff 26 during the pressurizing step for the pressing cuff 26, or may be performed based only on the detection results for the pressure P in the pressing cuff 26 during the depressurizing step for the pressing cuff 26.

Then, the control unit 21 generates the electrocardiographic waveform display data (S112). The control unit 21 generates the electrocardiographic waveform display data using only the detection results from the detection circuit 32 acquired during a period from the stoppage of pressurization of the pressing cuff 26 until the start of depressurization of the pressing cuff 26. The control unit 21 determines that, among the detection results from the detection circuit 32 during the period from the start of pressurization (S103) until the end of depressurization (S111), the detection results corresponding to the pressurizing step and the depressurizing step for the pressing cuff 26 are noise, and generates the electrocardiographic waveform display data reflecting only the detection results during the pressurized state maintaining step. The control unit 21 stores the generated electrocardiographic waveform display data in the electrocardiographic information storage unit 74 of the storage unit 22 as electrocardiographic measurement results.

Then, the control unit 21 causes the display unit 25 to display the blood pressure measurement results and the electrocardiographic measurement results (S113). The control unit 21 causes the display unit 25 to display, as the blood pressure measurement results, the systolic blood pressure and the diastolic blood pressure calculated during the calculation of the blood pressure (S111). Additionally, the control unit 21 causes the display unit 25 to display, as the electrocardiographic measurement results, the electrocardiographic waveform display data generated in the generation of the electrocardiographic waveform display data (S112).

2.5 Actions and Effects

Now, an example of actions and effects of the blood pressure measurement system according to the present embodiment will be described.

Figure 9:
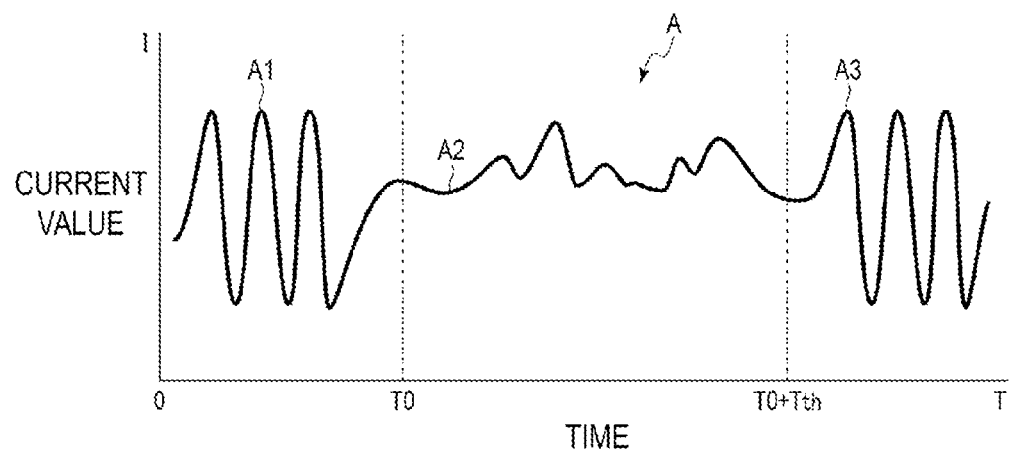
FIG. 9 is a diagram illustrating an example of acquired results for an electrocardiographic waveform from the blood pressure measurement circuit as an example of the measurement device according to the first embodiment.

FIG. 9 is a diagram illustrating an example of detection results from the detection circuit 32 during the electrocardiographic measurement processing illustrated in the example in FIG. 6. In the example in FIG. 9, the detection results from the detection circuit 32 include an electrocardiographic waveform A. The horizontal axis of the electrocardiographic waveform A indicates time T. Additionally, the vertical axis of the electrocardiographic waveform A indicates current I.

The electrocardiographic waveform A includes a first region A1, a second region A2, and a third region A3. The first region A1 is based on the detection results during the pressurizing step. The second region A2 is based on the detection results during the pressurized state maintaining step. The third region A3 is based on the detection results during the depressurizing step.

Here, as is known, in the electrocardiographic measurement, proper measurement results fail to be obtained when the electrodes are not in proper contact with the skin at the attachment site. For example, as illustrated in the example in FIG. 7, during the pressurizing and depressurizing steps for the pressing cuff 26, the second electrode 31 may fail to contact the wrist H of the user with sufficient contact strength. Thus, as illustrated in the example in FIG. 9, an unstable fluctuation is observed in the electrocardiographic waveform (first region A1) based on the detection results during the pressurizing step for the pressing cuff 26, and the electrocardiographic waveform (third region A3) based on the detection results of the depressurizing step for the pressing cuff 26, and these electromagnetic waveforms are preferably considered to be noise.

On the other hand, in the electrocardiographic measurement, proper measurement results can be obtained in a state where the electrodes are in proper contact with the skin at the attachment site. For example, as illustrated in the example in FIG. 8, in a state where the pressing cuff 26 sufficiently pressurized during the blood pressure measurement, the second electrode 31 is pressed toward the wrist H of the user with sufficient contact strength. Thus, as illustrated in the example in FIG. 9, relatively high stability is observed in the electrocardiographic waveform (second region A2) based on the detection results, for example, during the pressurized state maintaining step, i.e. during the period from the end of the pressurizing step before the start of the depressurizing step for the pressing cuff 26, and this electromagnetic waveform can be used as proper detection results.

In the present embodiment, the pressurized state maintaining step is provided between the pressurizing step and the depressurizing step for the pressing cuff 26. The electrocardiographic waveform display data is generated that reflects the detection results from the detection circuit 32 during the pressurized state maintaining step. In the pressurized state maintaining step, the detection results are acquired from the detection circuit 32 in a state where the second electrode 31 is properly pressed against the skin at the attachment site of the user due to expansion of the pressing cuff 26. In other words, according to the present embodiment, the state can be generated in which the electrocardiograph measurement electrodes are in proper contact with the attachment site of the user, and the electrocardiographic measurement can be performed with the electrocardiograph measurement electrodes in proper contact with the attachment site of the user.

In addition, in the present embodiment, the detection results are acquired from the detection circuit 32 during the period from the pressurizing step through the depressurizing step for the pressing cuff 26. In addition, among the acquired detection results, the detection results that correspond to the pressurizing step and the depressurizing step for the pressing cuff 26 are determined to be noise. Then, the electrocardiographic waveform display data is generated using only the detection results excluding the detection results that correspond to the pressurizing step and the depressurizing step for the pressing cuff 26. Thus, the display unit displays, as electrocardiographic measurement results, only the electrocardiographic data reflecting the detection results during the pressurized state maintaining step. Consequently, according to the present embodiment, the electrocardiographic waveform can be displayed that reflects only the detection results obtained while the electrocardiographic waveform is stable, that is, only the electrocardiographic data useful for diagnosis.

2.6 Modified Example

Note that the electrocardiographic measurement may be performed only in a state where the second electrode 31 of the blood pressure measurement device 10 is in proper contact with the attachment site of the user. In this modified example, the control unit 21 starts pressurizing the pressing cuff 26 without the supply of power to the first electrode 30 and the second electrode 31 or detection by the detection circuit 32, for example. Then, for example, after the pressurization of the pressing cuff 26 is stopped, the display unit 25 is caused to display the instruction to the user to perform the electrocardiographic measurement operation. Then, based on the execution of the electrocardiographic measurement operation, the supply of power to the first electrode 30 and the second electrode 31 is started to start the detection by the detection circuit 32. Then, based on the elapse of the electrocardiographic measurement time from the input of the electrocardiographic measurement operation, the supply of power to the first electrode 30 and the second electrode 31 is stopped and the depressurization of the pressing cuff 26 is started.

In the present modified example, the electrocardiographic measurement is started after the pressurization of the pressing cuff 26 is stopped, and the depressurization of the pressing cuff 26 is started after the elapse of the electrocardiographic measurement time. Thus, the detection results are acquired from the detection circuit 32 only during the period from after the stoppage of pressurization of the pressing cuff 26 before the start of the depressurization of the pressing cuff 26. Accordingly, the detection results are acquired from the detection circuit 32 only in a state where the second electrode 31 is properly pressed against the skin at the attachment site of the user due to expansion of the pressing cuff 26. Consequently, the electrocardiographic waveform display data can be generated using only the detection results obtained in a state where the electrocardiographic waveform is stable. According to the present modified example, the current for the electrocardiographic measurement flows through the user only during the time when the proper electrocardiographic measurement results can be acquired. Thus, the proper electrocardiographic waveform can be exclusively and effectively acquired without unnecessary extension of the time for which the current is flowing through the body of the user. This enables a reduction in physical burden on the user.

3. Common Configurations of Embodiments and the Like

A measurement device (1:10) includes a pressure acquisition unit (2:61) configured to acquire pressure information representing pressure in a pressing cuff, a cuff pressure control unit (3:63) configured to control, based on the pressure information, the pressure in the pressing cuff during each of a pressurizing step of pressurizing the pressing cuff, a pressurized state maintaining step of maintaining the pressing cuff in a pressurized state after end of the pressurizing step, and a depressurizing step of depressurizing the pressing cuff after end of the pressurized state maintaining step, a blood pressure calculation unit (4:62) configured to calculate a blood pressure of a user based on the pressure information, and an electrocardiographic measurement unit (5:65, 66) configured to measure an electrocardiogram of the user during the pressurized state maintaining step.

Note that the present invention is not limited to the embodiment, and various modifications can be made in an implementation stage without departing from the gist. Further, embodiments may be carried out as appropriate in a combination, and combined effects can be obtained in such case. Further, the various inventions are included in the embodiment, and the various inventions may be extracted in accordance with combinations selected from the plurality of disclosed constituent elements. For example, in a case where the problem can be solved and the effects can be obtained even when some constituent elements are removed from the entire constituent elements given in the embodiment, the configuration obtained by removing the constituent elements may be extracted as an invention.

Supplementary Notes

A part or the entirety of the embodiment can be described as described in the following supplementary notes in addition to the scope of the claims, but the present invention is not limited thereto.

(Supplementary Note 1)

A measurement device including a hardware processor (21) and a memory (22), wherein the hardware processor (21) is configured to
acquire pressure information representing pressure in a pressing cuff and cause the memory (22) to store the pressure information being acquired,
control, based on the pressure information stored in the memory (22), the pressure in the pressing cuff during each of a pressurizing step of pressurizing the pressing cuff, a pressurized state maintaining step of maintaining the pressing cuff in a pressurized state after end of the pressurizing step, and a depressurizing step of depressurizing the pressing cuff after end of the pressurized state maintaining step, calculate a blood pressure of a user based on the pressure information stored in the memory (22), and cause the memory (22) to store the blood pressure being calculated, and
measure an electrocardiogram of the user during the pressurized state maintaining step, and cause the memory (22) to store the electrocardiogram being measured.

REFERENCE SIGNS LIST

1 Blood pressure measurement device
2 Pressure acquisition unit
3 Pressing cuff control unit
4 Blood pressure calculation unit
5 Electrocardiographic measurement unit
6 Output unit
10 Blood pressure measurement device
11 Portable terminal
12 Physician terminal
13 Server
21 Control unit
22 Storage unit
23 Communication unit
24 Operation unit
25 Display unit
26 Pressing cuff
27 Pump
18 Pressure sensor
29 Battery
30, 31 Electrode
32 Detection circuit
32 Body
41A Front surface
41B Rear surface
42 Belt
42A Outward facing surface
42B Inward facing surface
43 Cuff unit
43A Outward facing surface
43B Inward facing surface
44, 45 Conductor
46 Push button
47, 48 Belt portion
61 Pressure acquisition unit
62 Blood pressure calculation unit
63 Pressing cuff control unit
64 Power control unit
65 Current acquisition unit
66 Electrocardiographic waveform generation unit
67 Output unit
71 Pressure information storage unit
72 Detection information storage unit
73 Blood pressure information storage unit
74 Electrocardiographic information storage unit
75 Setting information storage unit
A Electrocardiographic waveform

The invention claimed is:

1. A measurement device comprising:
a body including a first surface provided with a display and a second surface corresponding to a rear surface with respect to the first surface;
a belt attached to the body and configured to be wrapped around an attachment site of a user;
a pressing cuff attached to a side surface of the body and configured to extend between the belt and the attachment site of the user;
a processor configured to:
  acquire pressure information representing pressure in the pressing cuff;
  control, based on the pressure information, the pressure in the pressing cuff during each of a pressurizing step of pressurizing the pressing cuff, a pressurized state maintaining step of maintaining the pressing cuff in a pressurized state after an end of the pressurizing step, and a depressurizing step of depressurizing the pressing cuff after an end of the pressurized state maintaining step;
  calculate a blood pressure of the user based on the pressure information; and
  measure an electrocardiogram of the user during the pressurized state maintaining step; and
a first electrode and a second electrode as a pair of electrocardiographic electrodes, wherein
the processor is configured to maintain the pressure in the pressing cuff during the pressurized state maintaining step at a pressure at the end of the pressurizing step,
the second electrode is disposed at a position where the second electrode is configured to contact skin at the attachment site of the user in a state where the pressing cuff is attached to the user, the attachment site is a site to which the pressing cuff and the body are configured to be attached to, and the second electrode is disposed on the second surface of the body, and is configured to be pressed against the attachment site by the pressing cuff which is expanded during the pressurized state maintaining step.

2. The measurement device according to claim 1, wherein the processor is configured to set a duration of the pressurized state maintaining step to be equal to or longer than a measurement time required to obtain an electrocardiographic waveform useful for diagnosis.

3. The measurement device according to claim 1, wherein the processor is configured to calculate the blood pressure of the user based on a fluctuation in pressure in the pressing cuff during the pressurizing step or the depressurizing step, the fluctuation being acquired from the pressure information.

4. The measurement device according to claim 1, wherein the processor is further configured to:
acquire detection information representing a current value flowing through a heart of the user between the pair of electrocardiographic measurement electrodes; and
generate an electrocardiographic waveform reflecting the detection information during the pressurized state maintaining step based on the acquired detection information.

5. The measurement device according to claim 4, wherein the processor is further configured to:
acquire the detection information during a period from the pressurizing step through the depressurizing step; and
generate the electrocardiographic waveform reflecting only the detection information that is acquired during the pressurized state maintaining step, from among the detection information being acquired.

6. The measurement device according to claim 4, wherein the processor is further configured to acquire, as the detection information, only the current value during the pressurized state maintaining step.

7. The measurement device according to claim 4, wherein the first electrode is disposed at a position where the first electrode is configured to be in contact with an opposing finger to an arm of the user where the attachment site is located and does not contact the skin of the user at the attachment site in a state where the pressing cuff is attached to the user, the processor is further configured to detect, as the detection information, the current flowing through the heart of the user between the first electrode and the second electrode.

8. The measurement device according to claim 7, wherein the pressing cuff is configured to externally compress the attachment site of the user by being pressurized in the state where the pressing cuff is attached to the user, and the first electrode is disposed on the first surface of the body.

9. A measurement method for a measurement device including a body including a first surface provided with a display and a second surface corresponding to a rear surface with respect to the first surface; a belt attached to the body and configured to be wrapped around an attachment site of a user; a pressing cuff attached to a side surface of the body and extended between the belt and the attachment site of the user; and a first electrode and a second electrode as a pair of electrocardiographic electrodes to perform blood pressure measurement and electrocardiographic measurement of the user, the measurement method comprising the steps of:
acquiring pressure information representing pressure in the pressing cuff;
controlling, based on the pressure information, the pressure in the pressing cuff during each of a pressurizing step of pressurizing the pressing cuff, a pressurized state maintaining step of maintaining the pressing cuff in a pressurized state after an end of the pressurizing step such that the pressure in the pressing cuff is maintained at the pressure at the end of the pressurizing step, and a depressurizing step of depressurizing the pressing cuff after an end of the pressurized state maintaining step;
calculating a blood pressure of the user based on the pressure information; and
measuring an electrocardiogram of the user during the pressurized state maintaining step, wherein
the second electrode is disposed at a position where the second electrode contacts skin at the attachment site of the user in a state where the pressing cuff is attached to the user,
the attachment site is a site to which the pressing cuff and the body are attached to, and
the second electrode is disposed on the second surface of the body, and is pressed against the attachment site by the pressing cuff which is expanded during the pressurized state maintaining step.

10. A non-transitory recording medium having stored thereon a measurement program for causing a processor included in the measurement device to execute the steps of the measurement method of claim 9.

* * * * *